United States Patent
Faries, Jr. et al.

[19]

[11] Patent Number: 5,950,438
[45] Date of Patent: Sep. 14, 1999

[54] METHOD AND APPARATUS FOR MANIPULATING A SURGICAL DRAPE VIA AN INFLATABLE DEVICE TO COLLECT SURGICAL SLUSH

[75] Inventors: Durward I. Faries, Jr., McLean, Va.; Bruce R. Heymann, Silver Spring, Md.; Mark Licata, Richmond, Va.

[73] Assignee: O.R. Solutions, Inc., Chantilly, Va.

[21] Appl. No.: 09/038,012

[22] Filed: Mar. 11, 1998

Related U.S. Application Data

[62] Division of application No. 08/810,025, Mar. 4, 1997, Pat. No. 5,809,788
[60] Provisional application No. 60/012,832, Mar. 5, 1996.

[51] Int. Cl.[6] .................................................. F25C 5/06
[52] U.S. Cl. .................. 62/72; 62/353; 128/846
[58] Field of Search .............. 62/66, 340, 342, 62/72, 353; 128/846, 849

[56] References Cited

U.S. PATENT DOCUMENTS

| | | | |
|---|---|---|---|
| 2,277,605 | 3/1942 | Palitzsch | 219/43 |
| 2,778,921 | 1/1957 | Jepson | 219/44 |
| 3,155,260 | 11/1964 | Widener | 215/13 |
| 3,388,560 | 6/1968 | Moreland II | 62/72 |
| 3,739,595 | 6/1973 | Learn et al. | 62/353 |
| 3,902,484 | 9/1975 | Winters | 128/132 D |
| 4,393,659 | 7/1983 | Keyes et al. | 62/66 |
| 4,474,016 | 10/1984 | Winchell | 62/60 |
| 4,522,041 | 6/1985 | Menzel | 62/342 |
| 4,782,835 | 11/1988 | Bernardini | 128/403 |
| 4,869,271 | 9/1989 | Idris | 128/853 |
| 4,903,710 | 2/1990 | Jessamine et al. | 128/849 |
| 4,922,723 | 5/1990 | Broadbent | 62/353 |
| 4,934,152 | 6/1990 | Templeton | 62/342 |
| 4,967,061 | 10/1990 | Weber, Jr. et al. | 219/438 |
| 5,040,699 | 8/1991 | Gangemi | 222/1 |
| 5,042,455 | 8/1991 | Yue et al. | 126/263 |
| 5,129,033 | 7/1992 | Ferrara et al. | 392/447 |
| 5,163,299 | 11/1992 | Faries, Jr. et al. | 62/342 |
| 5,174,306 | 12/1992 | Marshall | 128/849 |
| 5,310,524 | 5/1994 | Campbell et al. | 422/33 |
| 5,331,820 | 7/1994 | Faries, Jr. et al. | 62/342 |
| 5,333,326 | 8/1994 | Faries, Jr. et al. | 4/639 |
| 5,363,746 | 11/1994 | Gordon | 99/328 |
| 5,374,813 | 12/1994 | Shipp | 235/375 |
| 5,383,476 | 1/1995 | Peimer et al. | 128/849 |
| 5,386,835 | 2/1995 | Elphick et al. | 128/849 |
| 5,400,267 | 3/1995 | Denen et al. | 364/552 |

(List continued on next page.)

*Primary Examiner*—William E. Tapolcai

[57] ABSTRACT

A surgical drape for use in a thermal treatment system congealing a sterile medium within a basin and automatically dislodging the congealed sterile medium adhered to the drape adjacent basin walls is accomplished by a drape having a drape portion covering the system housing with part of the drape portion disposed in the basin. The drape may further include a pre-formed container portion fitted to match the contour of, and being disposed within, the basin. The container portion may accommodate various shaped basins and include individual fluted sections, drape deformities, or an inflatable bladder surrounded by the fluted sections for facilitating dislodgement of the congealed medium. Further, the drape or preformed container portion may include a substantially annular bladder, or a bladder having a plurality of individually inflatable sections for manipulation of the drape relative to the basin to dislodge the congealed sterile medium. Alternatively, the bladders may be disposed between the drape or container portion and bottom of the basin for manipulation of the drape as described above. Moreover, the drapes may include stirrups to secure the drape to the system. A pump or bellows inflates and deflates the bladders via a piston having a reciprocating motion within a chamber, or, alternatively, via separate connections for inflation and deflation which are controlled by selective actuation of solenoids. The individually inflatable sections are inflated and deflated one section at a time in sequential order to manipulate the drape relative to the basin to dislodge the congealed sterile medium.

14 Claims, 10 Drawing Sheets

U.S. PATENT DOCUMENTS

| | | | |
|---|---|---|---|
| 5,400,616 | 3/1995 | Faries, Jr. et al. | 62/342 |
| 5,402,644 | 4/1995 | Faries, Jr. et al. | 62/3.6 |
| 5,429,801 | 7/1995 | Faries, Jr. et al. | 422/41 |
| 5,435,322 | 7/1995 | Marshall | 128/849 |
| 5,443,082 | 8/1995 | Mewburn | 128/897 |
| 5,449,892 | 9/1995 | Yamada | 235/462 |
| 5,457,962 | 10/1995 | Faries, Jr. et al. | 62/342 |
| 5,463,213 | 10/1995 | Honda | 235/468 |
| 5,502,980 | 4/1996 | Faries, Jr. et al. | 62/342 |
| 5,522,095 | 6/1996 | Faries, Jr. et al. | 4/639 |
| 5,524,478 | 6/1996 | Joy et al. | 73/40 |
| 5,524,643 | 6/1996 | Faries, Jr. et al. | 128/849 |
| 5,539,185 | 7/1996 | Polster | 219/439 |
| 5,551,240 | 9/1996 | Faries, Jr. et al. | 62/3.6 |
| 5,615,423 | 4/1997 | Faries, Jr. et al. | 4/639 |
| 5,653,938 | 8/1997 | Faries, Jr. et al. | 422/3 |

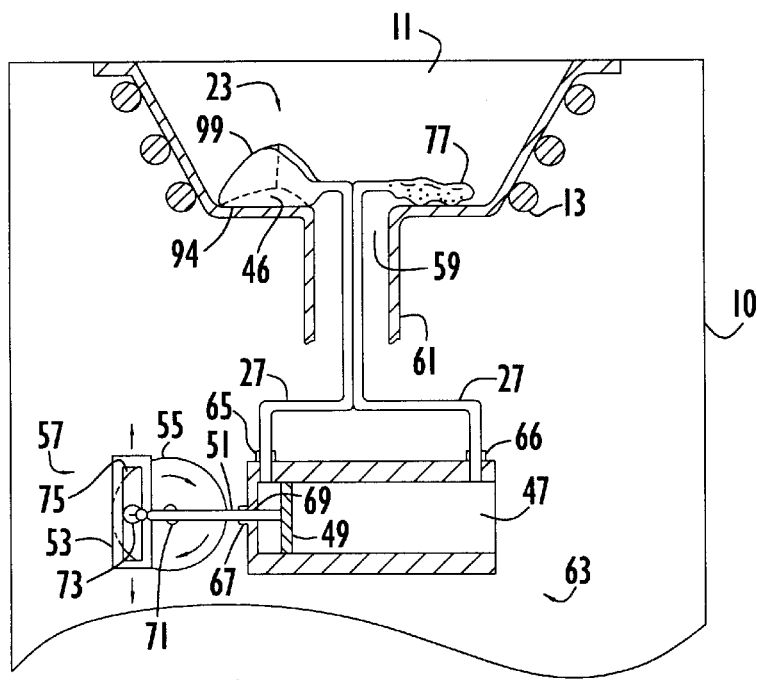
FIG.7a
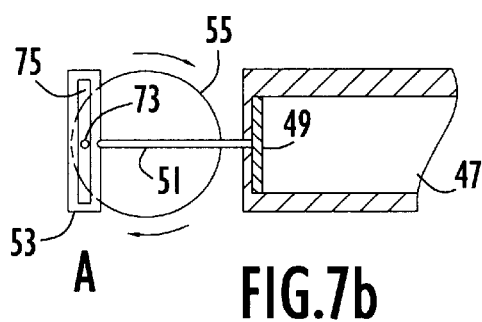
A  FIG.7b
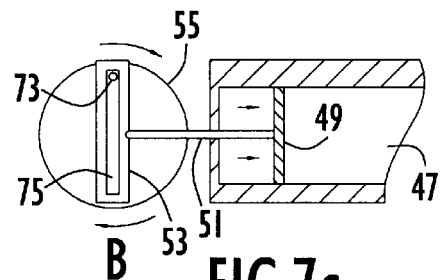
B  FIG.7c
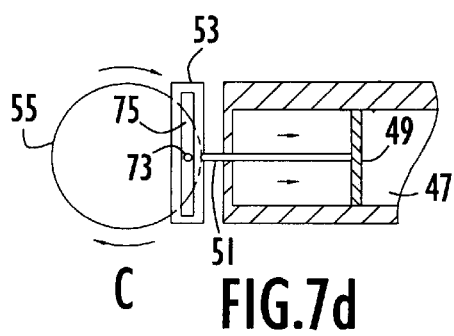
C  FIG.7d
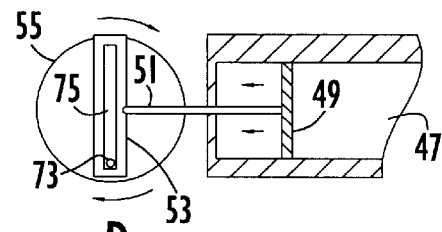
D  FIG.7e

METHOD AND APPARATUS FOR MANIPULATING A SURGICAL DRAPE VIA AN INFLATABLE DEVICE TO COLLECT SURGICAL SLUSH

CROSS-REFERENCE TO RELATED APPLICATIONS

This application is a divisional application of U.S. patent application Ser. No. 08/810,025, entitled "Surgical Drape for Use in Forming and Collecting Surgical Slush", filed Mar. 4, 1997, now U.S. Pat. No. 5,809,788which claims priority from U.S. Provisional patent application Ser. No. 60/012,832, entitled "Surgical Drape for Use in Forming and Collecting Surgical Slush", filed Mar. 5, 1996. The disclosures of the foregoing patent applications are incorporated herein by reference in their entireties.

BACKGROUND OF THE INVENTION

1. Technical Field

The present invention pertains to improvements in methods and apparatus for producing and collecting sterile slush. In particular, the invention is an improvement in the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al), 5,400,616 (Faries, Jr. et al), 5,502,980 (Faries, Jr. et al) and the patents cited therein. The disclosures in the aforementioned patents are expressly incorporated by reference herein in their entireties. In addition, the present invention relates to subject matter disclosed in co-pending U.S. patent application Ser. No. 08/810,104 filed Feb. 25, 1997, entitled "Surgical Drape for Use with Surgical Slush Machines Having an Automatic Dislodgement Mechanism".

2. Discussion of Prior Art

The above-referenced Keyes et al patent discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basins exterior and the liquid thermal transfer media to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent, the Keyes et al system has a number of disadvantages. In particular, the separate product basin must be removed and resterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush. The Faries, Jr. et al patent (U.S. Pat. No. 5,163,299) notes that scraping congealed liquid from the drape is undesirable in view of the potential for damage to the drape, resulting in a compromise of sterile conditions. In a solution to the problem, the patent proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The aforesaid Faries, Jr. et al patents (U.S. Pat. Nos. 5,502,980, 5,400,616 and 5,331,820) address the problem of removing the congealed liquid from the sides of the conformed drape receptacle in a surgical slush machine. Specifically, the drape is conformed to a cooled basin to establish a sterile field above the basin. The conformed drape receptacle collects a congealed sterile liquid (e.g. saline) in a sterile slush-like consistency. The congealed liquid tends to attach to sides of the drape receptacle in large clumps or pieces rather than automatically collecting within the drape receptacle interior. The Faries, Jr. et al patents (U.S. Pat. Nos. 5,502,980, 5,400,616 and 5,331,820) disclose several techniques for automatically manipulating the drape relative to the basin wall to thereby cause the congealed liquid to detach from the drape receptacle sides and collect interiorly as desired slush. Some of the techniques include: reciprocating the bottom of the conformed drape receptacle up and down, disposing a plate on the drape for reciprocating the bottom of the conformed drape receptacle up and down, alternately twisting the bottom of the drape receptacle in opposite directions, lifting portions of the drape receptacle away from the basin wall by use of a wobble plate or disk, employing rollers to separate the drape receptacle from the basin wall, utilizing a hoop or ring disposed about the basin periphery to manipulate the drape receptacle, inflating and deflating a bladder situated between the basin and the lowermost portion or bottom of the drape receptacle, and pressurizing and aspirating the space between the sides of the drape receptacle and basin wall.

The present invention is an improvement in the configuration of drapes used as surgical slush receptacles, and in techniques for separating drape receptacle sides from the basin wall in order to dislodge congealed liquid from the drape. The surgical drapes, described in the Faries, Jr. et al patents as utilized in surgical slush machines to ensure sterility and dislodge congealed slush, although effective for their intended function, can stand some improvement. For example, there is no provision to secure these drapes to a surgical slush machine cabinet or housing; nor is there any indication on the drape as to which portion of the drape should be inserted into the basin. The result is an increased possibility of drape displacement and/or improper alignment of the drape on the housing. Moreover, the drapes do not have the capability of regulating the size of fragments of congealed liquid forming on the drape sides. Specifically, the smooth and continuous interior surface of the drape permits large and unusable fragments of congealed liquid to form and collect in the drape receptacle. These fragments require some intervention to be broken down into a slush consistency.

The technique disclosed in the above-referenced Faries et al patents for separating the conformed drape receptacle from the basin wall by the utilization of a bladder can also stand some improvement. Specifically, that bladder only has the capability of manipulating the drape at a single location, at a certain angle, and in a certain direction. Further, that bladder-driven drape has no provision for manipulation of substantial portions of the drape, thereby causing significant clumps of congealed liquid to remain on the unmanipulated drape portions.

OBJECTS AND SUMMARY OF THE INVENTION

Accordingly, it is an object of the present invention to provide a drape contoured to be easily deployed as a drape container in a basin forming part of a surgical slush machine.

It is another object of the present invention to provide an improved selectively inflatable bladder arrangement for use with a drape container in a surgical slush machine basin to more efficiently dislodge frozen sterile medium from the drape container sidewalls.

It is also an object of the present invention to provide an improved sterile drape for use as a container in a surgical slush machine basin wherein the drape includes a drape portion to cover the cabinet or housing of the machine and a pre-formed receptacle portion contoured to match the contour of the basin in order to precisely fit into the basin.

It is another object of the present invention to provide an improved sterile drape for use as a container in a surgical slush machine basin recessed in a top surface of the machine wherein the drape forms a drape receptacle or includes a pre-formed container portion contoured to match the contour of the basin and wherein a substantially annular bladder is part of the bottom of the drape receptacle or container portion. The bladder is alternately inflated and deflated to manipulate the drape sides and dislodge congealed sterile liquid adhering to the drape receptacle or container portion. Alternatively, the substantially annular bladder may be a separate unit disposed between the drape receptacle or container portion and bottom of the basin for manipulation of the drape.

It is a further object of the present invention to provide an improved sterile drape for use as a container in a surgical slush machine basin wherein the drape includes a preformed container portion fitted to match the contour of the basin, and wherein a substantially annular bladder is provided with a plurality of individually formed fluted sections disposed about the bladder. The edges of the fluted sections are spaced from the basin and cause the congealed liquid to form as separate pieces that are more easily dislodged from the container sidewall while the bladder manipulates the drape.

It is another object of the present invention is to provide an improved sterile drape for use as a container in a thermal treatment system basin for cooling and/or heating a sterile liquid wherein the drape includes stirrups or the like disposed at the drape corners in order to secure the drape to the corresponding corners of the system cabinet or housing.

Still another object of the present invention is to provide an improved sterile drape for use as a receptacle for slush in a surgical slush machine basin and having a pre-formed container portion contoured to fit in the basin with a plurality of individually formed fluted sections disposed about the receptacle collectively fitted to generally match the basin contour. The fluted sections cause the congealed liquid to form as separate pieces that are more easily dislodged from the receptacle sidewall.

Yet another object of the present invention is to provide an improved sterile drape, for use as a container in a surgical slush machine basin, including a bladder having a plurality of individually inflatable sections. The inflatable sections are part of either a drape receptacle formed by the drape in the basin or a preformed container portion disposed in the drape with the sections inflated and deflated one section at a time to effect manipulation of the drape. Alternatively, the bladder may be disposed between the drape receptacle or container portion and the basin for manipulation of the drape.

A further object of the present invention is to provide an improved method and apparatus for automatically manipulating a sterile drape disposed in a basin of a surgical slush machine to dislodge congealed liquid adhered to the sides of the drape. The drape either forms a drape receptacle in the basin or has a pre-formed container portion, and includes a bladder with a plurality of individually inflatable sections disposed in the bottom of the drape receptacle or container portion. The inflatable sections are sequentially inflated and deflated via a pump employing, for example, either a reciprocating piston mechanism or actuation of solenoids to control fluid flow to the inflatable sections. Alternatively, the bladder may be disposed between the drape receptacle or container portion and the bottom of the basin to dislodge the congealed liquid by alternately inflating and deflating each of the sections, as described above, to manipulate the drape.

Still another object of the present invention is to provide an improved sterile drape for use as a container in a surgical slush machine basin wherein the drape has a drape portion covering the machine cabinet and a pre-formed container portion fitted to the basin contour and having deformities such as wrinkles or ridges disposed about the container portion perimeter. The wrinkles or ridges enable dislodgement of the congealed liquid from the sides of the pre-formed portion and limit the size of the congealed liquid fragments to those sizes capable of immediate use.

The aforesaid objects are achieved individually and in combination, and it is not intended that the present invention be construed as requiring two or more of the objects to be combined unless expressly required by the claims attached hereto.

According to the present invention, a sterile surgical drape, for use with a surgical slush machine having a basin recessed in a top surface of the machine, includes a drape portion placed over the machine cabinet or housing and hanging down from the top surface, and a pre-formed container portion fitted to match the contour of, and disposed within, the basin. Alternatively, the drape may include a continuous drape portion, part of which is disposed in the basin to form a drape receptacle. The container portion and basin may be of any perimetrical shape (e.g. polygonal, elliptical or oval, circular) and may further include a continuous sequence of inwardly concave fluted sections arranged to collectively conform generally to the basin shape. The edges of the fluted sections maintain a distance between the basin wall and liquid congealing on the sides of the pre-formed portion in order to ease dislodgement of the congealed liquid pieces from the sides of the container. In addition, a substantially annular integral and inflatable bladder may be disposed in the lowermost portion or bottom of the drape receptacle or container portion, or as a separate unit between the drape receptacle or container portion and the bottom of the basin, wherein the bladder is alternately inflated and deflated during operation of the machine to manipulate the drape and dislodge congealed liquid formed on the sides of the drape receptacle or container portion adjacent the basin walls. Further, the substantially annular integral bladder may include the individually fluted sections described above disposed about the bladder within the container portion of the drape.

A further embodiment of the surgical drape includes the drape receptacle or pre-formed container portion having a bladder including a plurality of individually inflatable sections disposed about the drape receptacle or container portion with the bladder being either integral with the drape at the bottom of the drape receptacle or container portion, or a separate unit positioned between the drape receptacle or container portion and the bottom of the basin. The individually inflatable sections are alternately inflated and deflated one section at a time in sequential order to manipulate the drape and dislodge congealed liquid formed on the sides of the drape receptacle or container portion.

In yet another embodiment, the surgical drape having either the drape receptacle or preformed container portion includes stirrups disposed at each corner of the drape to secure the drape to any thermal treatment system cabinet or housing.

An alternative pre-formed container portion of the drape in still another embodiment includes a plurality of wrinkles or ridges disposed about its perimeter. The lowermost or bottom part of the container portion may be either non-planar or smooth. The wrinkles or ridges may be spaced in any fashion about the container portion perimeter and may have any desired transverse width for determining the amount of contact between the basin walls and the container portion of the drape. The reduced contact with the basin walls diminishes the force attracting the congealed liquid to the sides of the pre-formed portion, thereby easing dislodgement of the congealed liquid. Further, the wrinkles or ridges limit the size of the congealed liquid fragments forming on the sides of the container portion, thereby eliminating the additional task of breaking up large congealed liquid fragments to the proper size for practical use.

The apparatus for utilizing the aforementioned drapes are typically of the types disclosed in U.S. Pat. Nos. 5,502,980, 5,400,616 and 5,331,820 and may further include a pump or bellows for inflating and deflating any of the aforementioned inflatable embodiments. The pump or bellows may be of the type whose inflation and deflation modes are controlled by the polarity of voltage on the input terminals of the pump or bellows. Alternatively, and especially for use with embodiments having the aforementioned individually inflatable sections, the pump or bellows may employ either a reciprocating piston mechanism, or a mechanical or electrical control device for selective actuation of solenoids controlling fluid flow to the particular inflatable embodiment, thereby enabling inflation and deflation of the inflatable sections one section at a time in sequential order.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

BRIEF DESCRIPTION OF THE DRAWINGS

FIG. 7a is an elevational view in partial section of a bladder with two individually inflatable sections disposed at the lowermost portion or bottom of a basin in a surgical slush machine having a reciprocating piston mechanism for individually inflating and deflating the inflatable sections according to the present invention.

FIGS. 7b–7e are elevational views in partial section of the reciprocating piston mechanism of the surgical slush machine of FIG. 7a illustrating the motion sequence of the piston during inflation and deflation of the individually inflatable sections according to the present invention.

DESCRIPTION OF THE PREFERRED EMBODIMENTS

Figure 1:
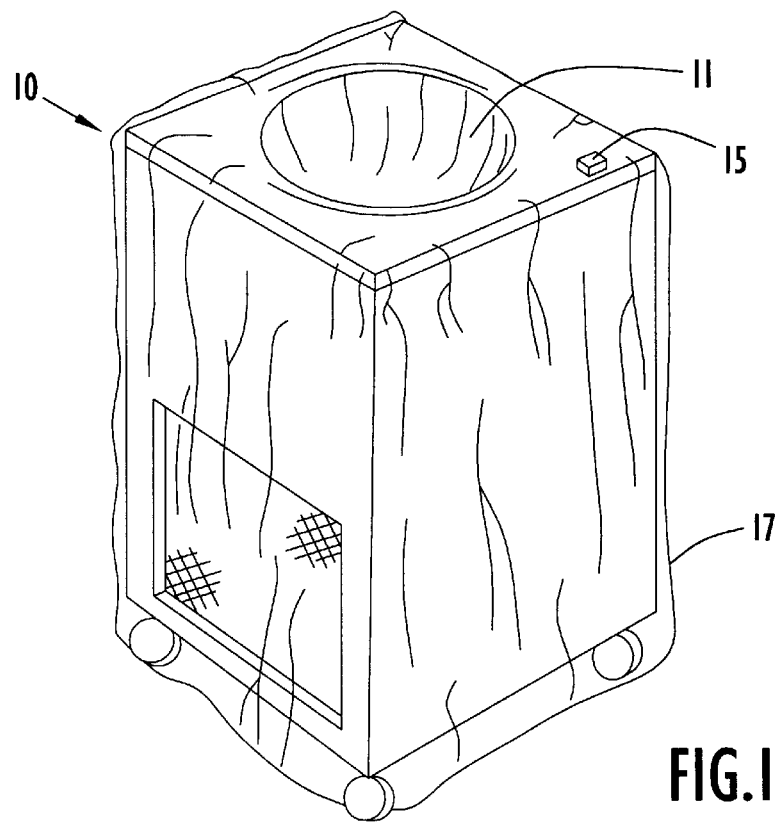
FIG. 1 is a view in perspective of a surgical slush machine and drape of the type employed in the present invention.
Figure 5A:
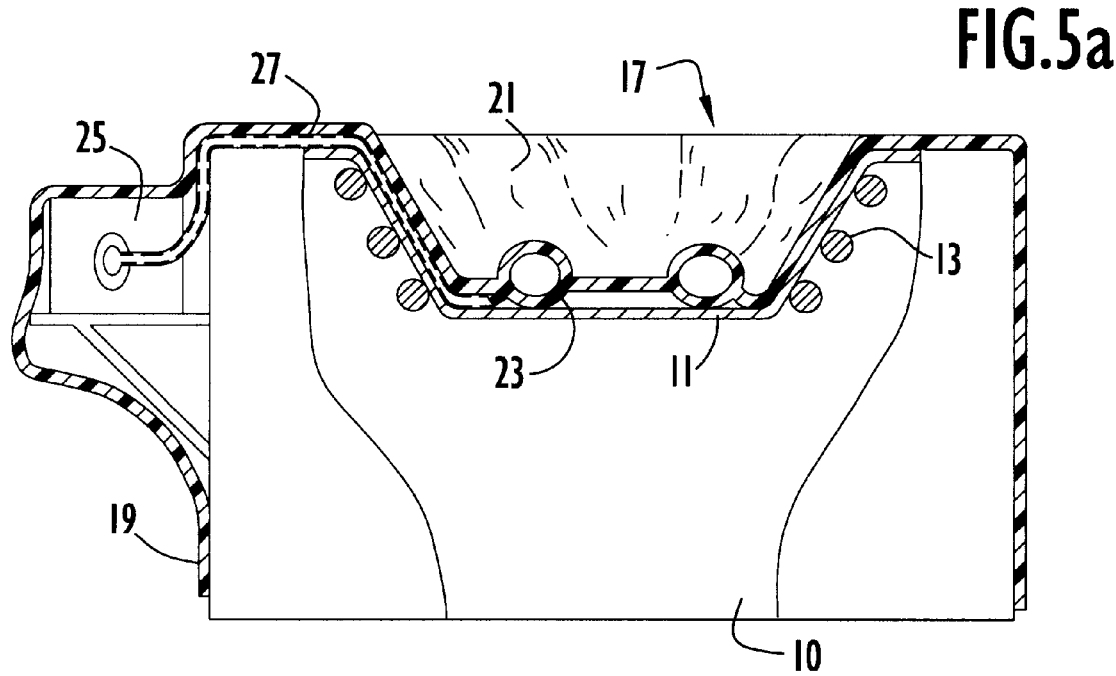
FIG. 5a is an elevational view in partial section of a drape including a drape receptacle or container portion having a substantially annular inflatable bladder wherein the receptacle or container is disposed in a basin of a surgical slush machine having a pump or bellows for inflating and deflating the bladder according to the present invention.
Figure 9D:
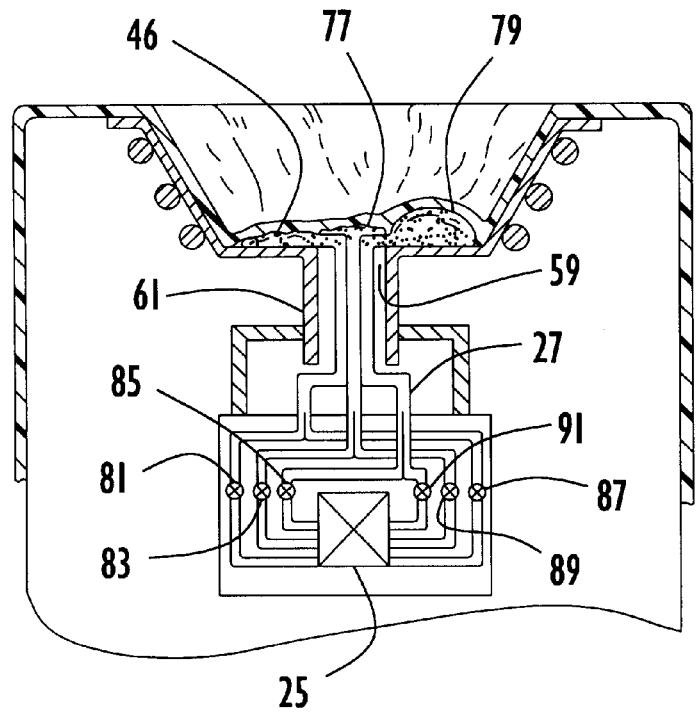
FIGS. 9b–9d are elevational views in partial section of the bladder and basin of FIG. 9a covered by a surgical drape illustrating the sequence of inflation and deflation of the individually inflatable sections according to the present invention.

Referring to FIGS. 1 and 5a, a surgical slush generating system of the type employed by the present invention and described in the above-referenced Templeton patent includes a cabinet or housing 10 with a top surface having a basin 11 mounted thereon in an appropriately sized recess. Basin 11 is made of a thermally conductive material, typically stainless steel, and includes a generally flat bottom wall and frusto-conical side wall. A conventional refrigeration unit is disposed within cabinet or housing 10 and typically includes a compressor, a condenser and an expansion control unit connected by appropriate fluid conduits that close the refrigeration loop with an evaporator 13. The evaporator is in the form of a coil wound about the exterior surface of basin 11 in thermal transfer relation therewith. When the refrigeration unit is activated via appropriate controls 15, evaporator 13 cools the side wall of basin 11 to a temperature substantially below the freezing temperature of the liquid used in forming the sterile slush. The temperature is preferably on the order −30° F. to 10° F. For further details of the structure and operation of the refrigeration unit, reference is made to the aforementioned Keyes et al and Templeton et al patents.

A sterile drape 17, preferably transparent, is disposed over the top and sides of cabinet or housing 10 and made to conform to the side wall and bottom of basin 11. The portion of drape 17 disposed in the basin serves as a sterile receptacle for sterile liquid placed therein to be frozen into the desired sterile slush. Typical sterile liquid used for this purpose is a 0.80% to 0.95% sodium chloride solution (i.e., saline). Drape 17 is made from a material that is impervious to the sterile liquid and sufficiently soft and flexible to conform to the basin wall. The thickness of the drape is preferably minimized to render thermal transfer therethrough most efficient yet the thickness is sufficient to resist tearing and puncturing during normal use. By way of example only, the drape may be made of materials commonly used in hospitals for surgical drapes and has a thickness in the range of 3.0 to 10.0 mils. Drape 17 may also be made of polyurethane film as disclosed for the drape in the aforementioned Templeton patent. The drape is designed to be disposable after a single use and is provided presterilized and prepackaged in a manner to preserve its sterile state during storage. The particular drape illustrated in FIG. 1 is contoured to match and be fitted over the top and side surfaces of cabinet 10. It is to be understood, however, that such fitted drapes can be replaced with loosely hanging drapes when exploiting the principles of the present invention.

In addition, the drape may have a pre-formed container portion 21 fitted to match the contour of and be disposed within basin 11 of the surgical slush machine. Basin 11 and/or container portion 21 may be of any functional shape including but not limited to polygonal (i.e., triangle, rectangle, square, pentagon etc.), elliptical or oval, or circular. Container portion 21 may be thicker than the remaining portions of the drape described above in order to resist puncture and enable the container portion to maintain the shape of the basin. Container portion 21 may be constructed as a separate unit and attached to the drape through an opening defined in the drape by heat welding or other types of attachment processes. By way of example only, portion 21 may be made of a heavy gauge polyethylene/ionomer resin blend having a thickness of approximately ten through sixteen mils. The percentage of the ionomer resin in the blend is approximately in the range between forty and seventy percent.

Figure 2A:
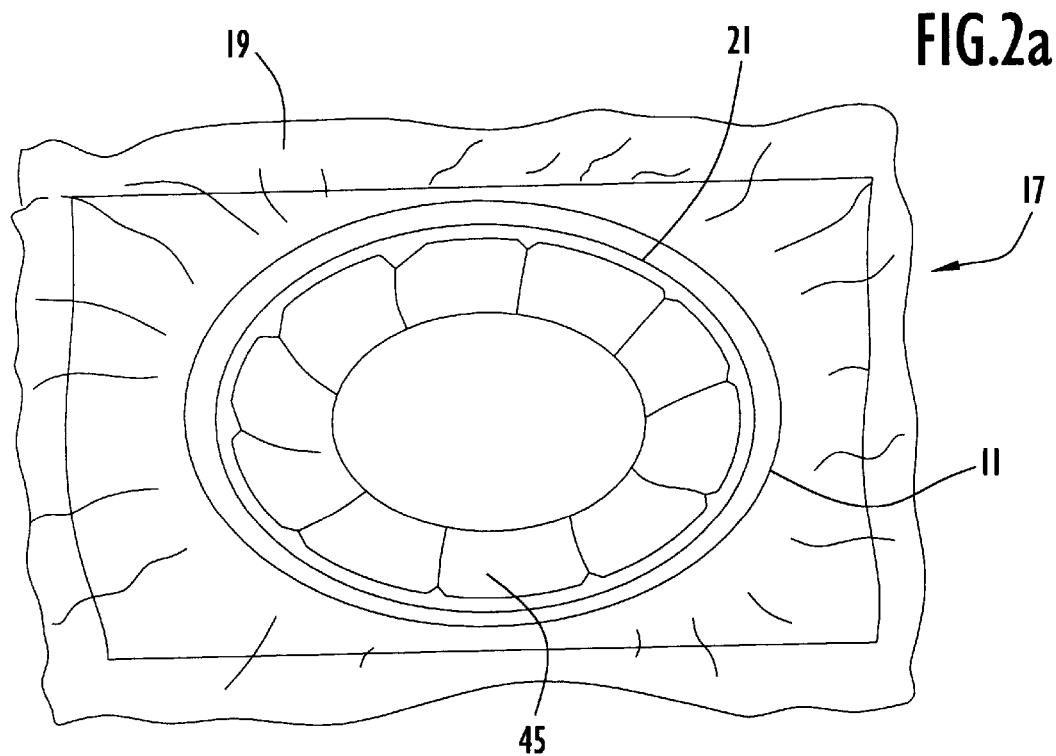
FIG. 2a is a top view in plan of a surgical drape having an elliptical or oval pre-formed container portion including individual fluted sections wherein the container is disposed in an elliptical or oval basin of a surgical slush machine according to the present invention.
Figure 2B:
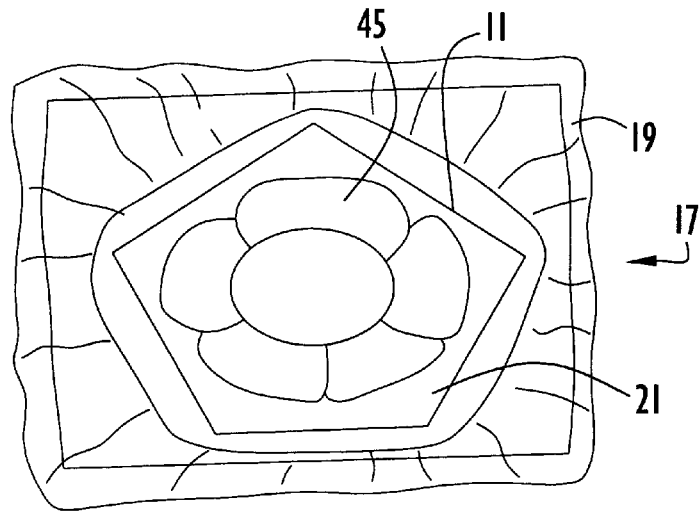
FIG. 2b is a top view in plan of a surgical drape having a pentagonal pre-formed container portion including individual fluted sections wherein the container is disposed in a pentagonal basin of a surgical slush machine according to the present invention.

During operation of the surgical slush machine, the sterile liquid in the drape container freezes in fragments on the sidewalls of that container. In order to easily dislodge these frozen fragments so as to more readily form sterile slush within the drape container, the pre-formed container portion 21 of the drape is provided with individual fluted sections 45 as illustrated in FIGS. 2a–2b. Specifically, drape 17 is substantially similar to the drape described above but further includes a series of the fluted sections 45 disposed in an endless sequence to define the container portion perimeter. Sections 45 are concave inward, convex outward, and are collectively fitted to generally match the contour of basin 11 (shown oval in the embodiment of FIG. 2a and pentagonal in the embodiment of FIG. 2b) and to space parts of the container portion (i.e., the junctions of the fluted sections) from the basin walls. The spacing between parts of the container portion 21 and the walls of basin 11 assures that the liquid congeals in smaller pieces since freezing typically occurs at the drape portions contacting the basin wall. The smaller pieces are more readily removed from the drape since the adhering force is relatively small. The drape container portion is not limited to the specific oval configuration described above but may be formed to accommodate any shaped basin (e.g., polygonal, oval or elliptical, circular etc).

Fluted sections 45 preferably extend vertically from the bottom to slightly below the top of container 21. Each fluted section 45 is positioned between and adjoins two other such sections, thereby forming a continuous or endless wall serving as the container perimeter. The bottom of container 21 has the general shape of the bottom of basin 11 and is defined by the bottom edges of individual fluted sections 45. The top edge of each fluted section 45 is substantially rounded, concave inward, to define a scalloped upper edge of container 21. The vertical sides of sections 45 are arcuate in respective vertical planes and project inwardly into container 21 to provide the spacing for segments of the container away from the wall of basin 11. For example, container 21 for an oval basin 11 (FIG. 2a) has an oval bottom formed by bottom edges of the fluted sections 45. Similarly, and by way of example, pre-formed container portion 21 for a pentagonal basin 11 (FIG. 2b) has a bottom in the shape of a pentagon with rounded edges defined by the bottom edges of the fluted sections 45.

Fluted sections 45 are pre-formed in the walls of container portion 21. The vertical edges of individual sections 45 correspond to pinches in the wall of the container portion while the parts of the drape disposed between the pinches is molded to form the concave inward, convex outward flutes. The fluted contour of the container portion may be viewed as similar to the contour of a bundt cake pan.

Figure 3A:
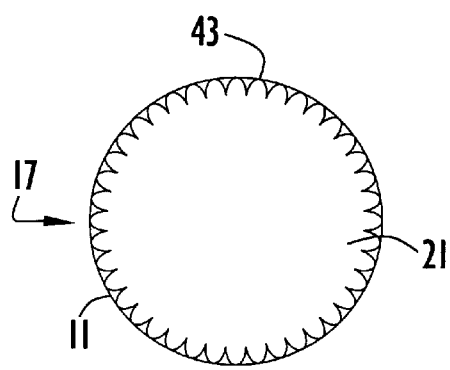
FIG. 3a is a top view in plan of a pre-formed container portion of a surgical drape including substantially evenly spaced wrinkles or ridges, the container being shown disposed in a basin of a surgical slush machine according to the present invention.

Alternative embodiments of the drape including other types of drape deformities, such as wrinkles or ridges 43, disposed about the perimeter of pre-formed container portion 21 are illustrated in FIGS. 3a–3d. Specifically, drape 17 is substantially similar to the drape having a container portion described above except that container portion 21 includes a plurality of drape deformities 43 disposed in the walls and about the perimeter of the container portion. Drape deformities 43 extend from the bottom to the top of, and are defined in the walls of, container portion 21 in several variations. For example, all of the drape deformities 43 in a given drape may have substantially similar dimensions and be equally spaced about the perimeter of container portion 21 with each wrinkle 43 forming a peak extending away from the walls of container portion 21 toward the center of the container portion (FIG. 3a). The continuous sequence of drape deformities 43 has a top view similar to a circular sawtooth pattern extending along the perimeter of the container portion. Drape deformities 43 are pre-formed in the walls of container portion 21. The peaks are formed as inwardly directed pinches in the walls of the container portion with the parts of the drape disposed between the pinches molded to form the concave inward, convex outward basin-contacting segments. The space between the pinches or peaks and the basin displaces the container portion from the basin wall to facilitate dislodgement of congealed liquid.

Figure 3B:
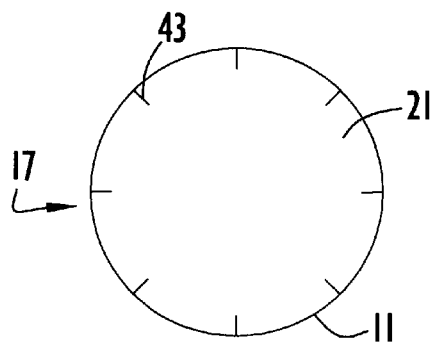
FIG. 3b is a top view in plan of a preformed container portion of a surgical drape including wrinkles or ridges spaced to provide maximal basin contact, the container being disposed in a basin of a surgical slush machine according to the present invention.

Another variation of ridges or wrinkles 43 includes a series of narrow drape deformities having substantially similar radial dimensions and equally spaced about the perimeter of container portion 21 (FIG. 3b). The drape deformities in FIG. 3b have a top view similar to spikes, pins or needles extending away from the container wall toward the center of the container portion. This arrangement provides for maximum contact area between the walls of container portion 21 and basin 11. The spikes are pre-formed as inward pinches in the walls of container portion 21 with the parts of the drape disposed between the pinches left intact to contact the basin.

Figure 3C:
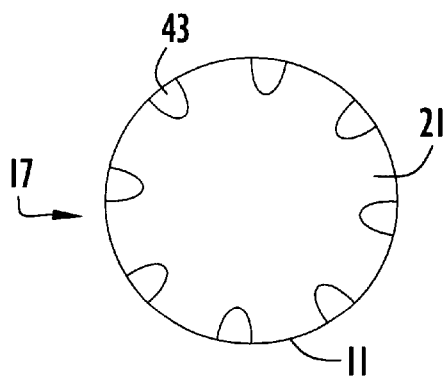
FIG. 3c is a top view in plan of a pre-formed container portion of a surgical drape including wrinkles or ridges spaced a substantial distance apart, the container being disposed in a basin of a surgical slush machine according to the present invention.
Figure 3D:
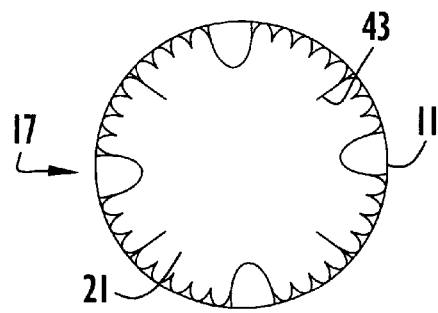
FIG. 3d is a top view in plan of a pre-formed container portion of a surgical drape including a combination of the wrinkle or ridge patterns of the drapes of FIGS. 3a–3c, the container being disposed in a basin of a surgical slush machine according to the present invention.

Yet another configuration variation for drape deformities 43 includes rounded inwardly directed peaks as illustrated in (FIG. 3c). These individual drape deformities 43 have a top view similar to parabolas tapering away from the walls of container portion 21 toward the center of the container portion. The rounded peaks are pre-formed in the walls of container portion 21 by displacing the drape inward to form the peaks with the parts of the drape disposed between the peaks left intact to contact the basin. A still further variation of drape deformities may take the form of any combination or permutation of the aforementioned variations described above and illustrated in FIG. 3d. These deformations in the container periphery are preformed in the walls of container portion 21 in substantially the same manner described above. Further, drape deformities 43 of any of the variations may be equally or randomly spaced and have uniform or varied radial and angular dimensions. Moreover, the dimensions of drape deformities 43 in the aforementioned embodiments may have any dimensions that accommodate the various distribution patterns.

The purposes of drape deformities 43, irrespective of the specific configuration, is to displace parts of container portion 21 from the walls of basin 11 to reduce the size of the congealed pieces and thereby reduce the force attracting the pieces to the container, facilitating their dislodgement.

Figure 4:
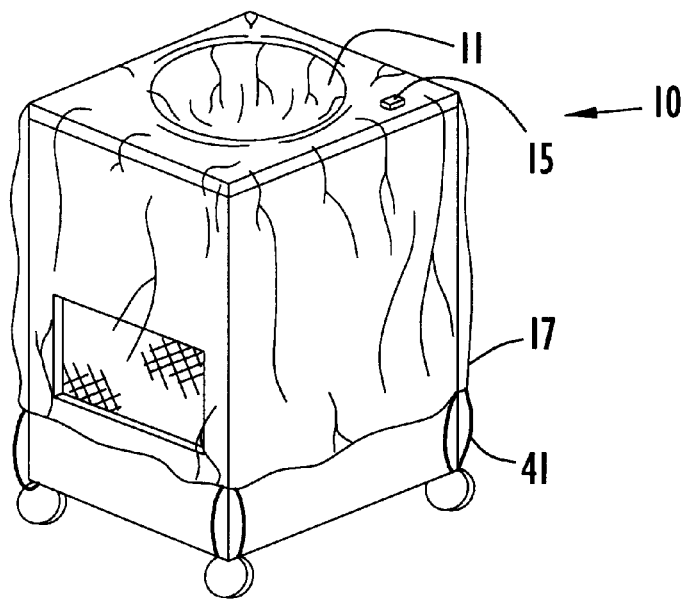
FIG. 4 is a view in perspective of a thermal treatment system for sterile media having a drape secured to the system cabinet or housing via stirrups disposed at corners of the drape according to the present invention.

A further embodiment of drape 17, including stirrups for securing the drape to any thermal treatment system, is illustrated in FIG. 4. This drape may be fitted to the cabinet or not, and have a preformed container or may be simply pushed down into and conformed to a basin to form a drape receptacle. This drape includes stirrups 41 disposed and extending from each of the corners of the drape. Stirrups 41 are preferably made of elastic or other rubber-band like material and are typically, although not necessarily, in the form of a loop adapted to engage either a castor or a bottom corner of system cabinet 10. After placing drape 17 over the cabinet such that the drape hangs over the top surface and extends down along the cabinet sides, stirrups 41 are secured about respective bottom corners of the cabinet to secure the drape in place.

In order to automatically dislodge congealed sterile liquid formed on the drape receptacle side walls 21 and collect the congealed liquid as sterile slush within the receptacle, the drape may include an inflatable bladder 23 to manipulate the drape. Referring to FIG. 5a, a drape 17 includes drape or cover portion 19, covering the top surface and hanging down over a pump 25 and the sides of cabinet or housing 10, and a drape receptacle portion 21 disposed in basin 11. A bladder 23 is approximately centered at the bottom of drape receptacle portion 21 adjacent the basin floor once the receptacle portion is properly positioned within basin 11. Bladder 23 is a substantially annular tubular member similar in shape to a tire inner tube or doughnut when inflated by a pump or bellows 25. Bladder 23 is preferably formed integral with, and of the same material used for, container portion 21. Alternatively, the bladder may be a separate unit disposed between the drape receptacle portion and the basin bottom.

Pump 25 is mounted on the side of the cabinet in the embodiment of FIG. 5a, but may be located interiorly of the cabinet. The pump is connected to bladder 23 via hose 27 extending from the pump to the bladder. Hose 27 is a conventional hose for transporting fluids and may be made of rubber plastic or other suitable material. Pump 25 alternately and continually cyclically inflates and deflates bladder 23 when actuated. As a result, the side walls of the drape receptacle 21 are periodically moved away from the walls of basin 11, thereby breaking the frozen attachment of the congealed liquid to the basin through drape receptacle side walls and dislodging the congealed liquid. The dislodged congealed liquid collects as slush in the center of basin 11 for easy access without the need for manually manipulating the drape. Pump 25 may be any known or commercially available pump or other device for the inflation and deflation of bladder 23. Further, bladder 23 is typically inflated with air but any other fluid (i.e., liquid or gas) capable of moving the drape and dislodging the congealed liquid may be used.

Figure 6:
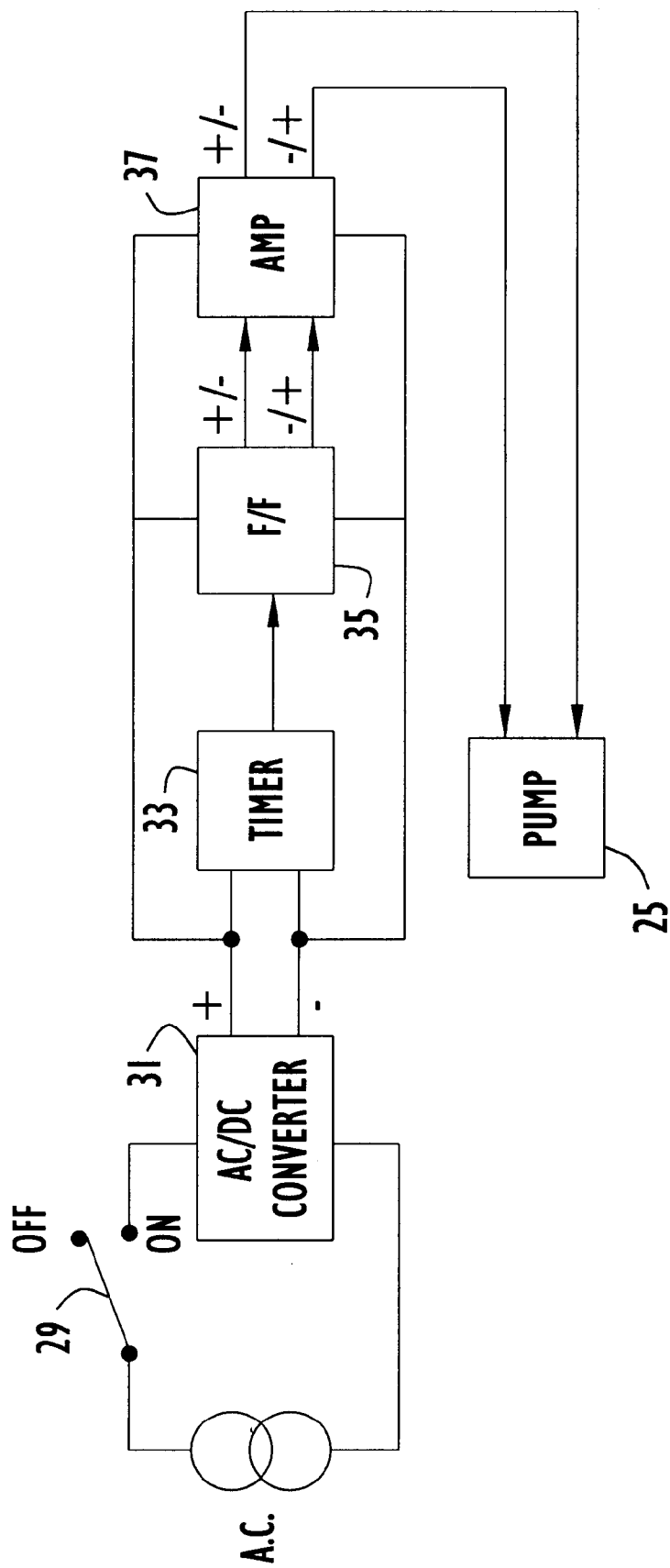
FIG. 6 is an electrical schematic diagram of an exemplary circuit for energizing the pump or bellows employed in the surgical slush machine of FIGS. 5a–5b.

The control of pump 25 to inflate and deflate bladder 23 is described with reference to the exemplary circuit of FIG. 6. Specifically, pump 25 may be of the type which provides either positive pressure or aspiration (i.e., negative pressure) from a single pressure port, depending upon the polarity of the voltage applied to the pump supply terminals. Alternatively, the pump may provide a differential pressure across two ports, the pressure polarity alternating with applied voltage polarity. Primary AC voltage is applied to an AC/DC converter 31 when a switch 29 is closed. Switch 29 may be actuated, for example, when the refrigeration power switch 15 (FIG. 1) is actuated. DC voltage from converter 31 is applied to a timer 33 arranged to continuously cycle to provide a series of output pulses at regular timed intervals (e.g. every five to thirty seconds). The output signal from timer 33 clocks a flip flop 35 of the type that responds to each pulse by changing the polarity of the voltage at its output signal lines. The output signal lines of flip flop 35 are connected to a driver amplifier 37 arranged to differentially amplify the alternating polarity voltages and alternately drive pump 25 between its two operating modes.

Figure 5B:
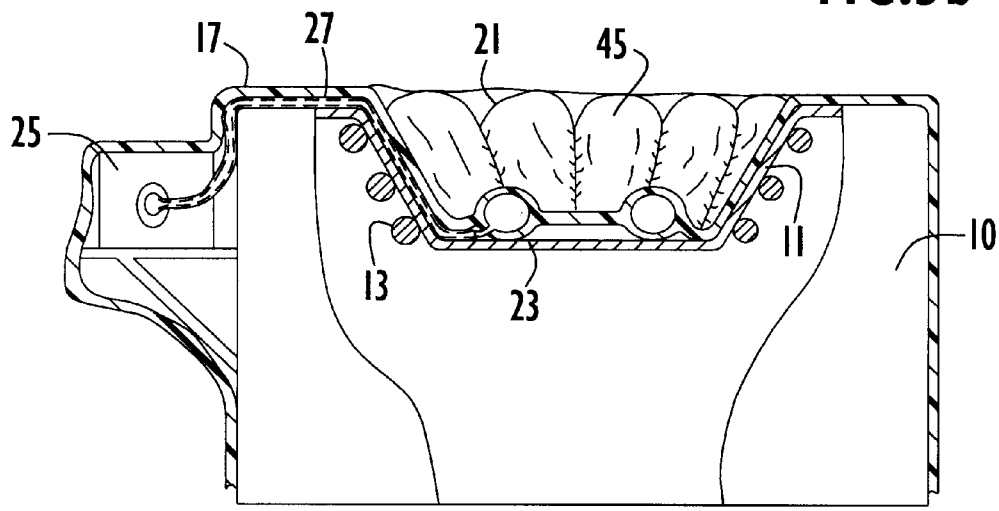
FIG. 5b is an elevational view in partial section of a surgical drape having a pre-formed container portion including a substantially annular bladder with individual fluted sections disposed about the bladder wherein the container is disposed in basin of surgical slush machine according to the present invention.

A drape manipulating bladder may be combined with individual fluted sections 45 formed in container portion 21 of a drape to further facilitate dislodgement of congealed liquid as illustrated in FIG. 5b. Specifically, container portion 21 includes substantially annular bladder 23 of the type described above, and a plurality of inwardly concave, outwardly convex, fluted sections 45 disposed about the bladder and collectively fitted to generally match the contour of container portion 21 and basin 11. Fluted sections 45 are substantially similar to the fluted sections (FIGS. 2a–2b) described above. A pump 25 is connected to bladder 23 via hose 27 to continuously cyclically inflate and deflate bladder 23 in substantially the same manner described. The inflation and deflation of bladder 23 manipulates container portion 21 relative to and away from the walls of basin 11 to facilitate dislodgement of congealed liquid. Since the fluted sections 45 maintain spacing between the segments of the container portion and the basin walls and thereby facilitate dislodgement in a manner substantially similar to the fluted sections described above, the combination of the bladder with the fluted sections provide enhanced dislodgement for collection of the congealed liquid as sterile slush.

A further technique for dislodging the congealed liquid from the drape includes employing a bladder 23 having a pair of individually inflatable sections 46, 77 wherein a separate bladder is disposed between the drape and the bottom of basin 11 for manipulation of the drape and dislodgement of congealed liquid as illustrated in FIG. 7a. Specifically, the drape container (not shown) is placed atop the bellows and may be preformed or otherwise. The bladder includes two individually inflatable sections 46, 77 pressurized alternately via motorized pump 63 employing a piston 49 driven by reciprocating mechanism 57. Bladder 23 may be made of rubber, the material used for the drape or other suitable material capable of retaining fluid. The individual sections 46, 77, in their respective fluid expanded states, have a substantially semi-annular or bellows shape (i.e., approximately one-hundred eighty degrees around) with a cross-section including an arcuate base 94 disposed flat against the basin floor and extending radially from the basin wall to an arc spaced a short distance from the basin center. An upper body 99 loosely overlies and is secured to base 94 and is amorphous when not inflated. Individual sections 46, 77 expand when inflated such that the highest point of upper body 99 relative to base 94 is approximately half the depth of the basin. Pump 63 alternately inflates and deflates each individually inflatable section 46, 77 differentially such that only one section is substantially fully inflated at any one time. The alternating inflation and deflation of the inflatable sections manipulates the drape relative to, and away from, the basin walls, thereby dislodging the congealed liquid from the drape as described above.

Each individually inflatable section 46, 77 is connected to pump 63 via hoses 27. Hoses 27 are conventional hoses and may be attached to the individual bladder sections via an opening defined at the radially inward edge of each inflatable section. Alternatively, hoses 27 may be integral with the inflatable sections and extend from the inflatable sections to the pump. Basin 11 includes an opening 59 defined at the approximate center of the bottom of the basin for receiving hose shaft 61 extending vertically to pump 63 disposed within the system cabinet. Hoses 27 connect inflatable bladder sections 46, 77 to respective ends of a piston chamber 47 in pump 63. Piston chamber 47 is substantially cylindrical and may be oriented such that its longitudinal axis is substantially perpendicular to hose shaft 61. Chamber 47 has opposite openings or ports 65, 66 defined in its exterior surface. Respective hoses 27 are connected to ports in openings 65, 66 for transporting fluid between pump chamber 47 and inflatable sections 46, 77. Piston 49 is a circular disk with a thickness slightly larger than the diameter of openings 65, 66. Piston 49 is concentrically disposed within chamber 47 and has a diameter slightly smaller than the chamber diameter. A shaft 51 is secured perpendicularly to and at the substantial center of the disk. Piston shaft 51 extends through a substantially circular opening 69 defined through the approximate center of a proximal end of chamber 47. Shaft 51 has a diameter slightly smaller than opening 69 and smoothly slides in a reciprocating manner along the longitudinal axis of chamber 47 through bearings 67, 71 disposed in opening 69 and at the approximate center of a drive wheel 55. Bearings 67, 71 are conventional bearings, typically ball bearings, or other suitable device, for enabling smooth reciprocating movement of shaft 51. Slotted drive block 53 is disposed at the proximal end of shaft 51 and transduces the rotary motion of drive wheel 55 to longitudinal movement of shaft 51 to drive piston 49 as described below.

The force driving shaft 51 and piston 49 originates from a configuration known as a "Scottish yoke". Specifically, drive wheel 55 is a substantially circular disk and has a diameter approximately one and one-half times that of chamber 47 with a thickness slightly greater than the thickness of piston 49. Drive wheel 55 rotates relative to bearings 71 about an axis disposed at the approximate center of the drive wheel wherein the axis is perpendicular to a plane of, and passes through, the drive wheel. Drive wheel 55 is positioned adjacent chamber 47 such that the longitudinal axis of chamber 47 is parallel to the plane of, and perpendicular to the axis of rotation of, drive wheel 55. Drive wheel 55 further includes roller 73 disposed just interiorly of the circumferential edge of drive wheel 55 and extending perpendicular to the plane of the drive wheel for engagement with a slotted drive block 53. Roller 73 is preferably a ball bearing or other rolling device capable of smooth traversal of a channel or surface. Drive wheel 55 rotates in a clockwise direction via application of a rotary force by a motor (not shown). Slotted drive block 53 is positioned adjacent drive wheel 55 and has a substantially rectangular cross-section with a straight linear channel 75 disposed at the approximate center and traversing substantially the entire longitudinal axis of the slotted drive block. Drive block 53 has a longitudinal length extending perpendicular to the longitudinal axis of chamber 47, approximately equal to the diameter of drive wheel 55. The thickness and transverse width of drive block 53 is slightly greater than the respective thickness and diameter of piston 49. Drive block 53 is connected to drive wheel 55 via engagement of roller 73 within channel 75. Channel 75 has a diameter slightly larger than the diameter of roller 73 to permit roller 73 to traverse channel 75 during rotation of drive wheel 55 as described below. Shaft 51 is connected to drive block 53 at the approximate center of the drive block. In other words, the piston configuration includes piston 49, shaft 51 and slotted drive block 53, all interconnected as described above. Drive wheel 55 includes only roller 73 which is disposed in channel 75 for transducing the rotary motion of drive wheel 55 to longitudinal motion of drive piston 49 in a reciprocating manner along the longitudinal axis of, and within, chamber 47.

Referring to FIGS. 7b–7e, operation of the driving mechanism is now described. Initially, piston 49 is positioned at the proximal edge of chamber 47 adjacent opening 65 (FIG. 7a) with roller 73 at the approximate center of channel 75, designated in FIG. 7b as position A. As drive wheel 55 rotates clockwise, roller 73 traverses longitudinal channel 75 along the longitudinal axis of slotted drive block 53 toward the proximal end of the drive block while applying a force to shaft 51 that is perpendicular to the drive block and along the longitudinal axis of shaft 51 in order to drive piston 49 toward the distal end of chamber 47. At position B (FIG. 7c), roller 73 is positioned at the upper end of drive block 53 with piston 49 driven approximately half-way toward the distal end of chamber 47. The rotary motion of drive wheel 55 has essentially two force components, namely an x-component and a y-component. The y-component drives roller 73 within channel 75 along the longitudinal axis of drive block 53 while the x-component drives roller 73 perpendicular to the longitudinal axis of the drive block to force piston 49 toward the distal end of chamber 47. In other words, the "Scottish yoke" utilizes the x-component of the rotary force to drive the piston.

As drive wheel 55 continues to rotate in a clockwise manner from position B, roller 73 traverses channel 75 toward the lower end of drive block 53 and continually drives piston 49 toward the distal end of chamber 47. At position C (FIG. 7d), roller 73 is again positioned at the approximate center of drive block 53 with piston 49 positioned adjacent opening 66 (FIG. 7a) at the distal end of chamber 47. Further clockwise rotation of drive wheel 55 causes roller 73 to traverse channel 75 until reaching the distal end of drive block 53 with piston 49 driven approximately half-way toward the proximal end of chamber 47, as shown at position D (FIG. 7e). The x-component of the rotary force is now in a reverse direction (one-hundred eighty degrees from the original direction) thereby driving piston 49 toward the proximal end of chamber 47. Similarly, additional clockwise rotation of drive wheel 55 causes the pump mechanism to return to position A, with roller 73 at the approximate center of drive block 53, and piston 49 at the proximal end of chamber 47. Therefore, the rotary motion of drive wheel 55 continuously drives piston 49 in a reciprocating manner along the longitudinal axis of, and within, chamber 47 for inflating and deflating the bladder as described below. Alternatively, drive wheel 55 may be rotated in a counter-clockwise direction to drive piston 49 in a reciprocating manner within chamber 47 in substantially the same manner described above.

Figure 8A:
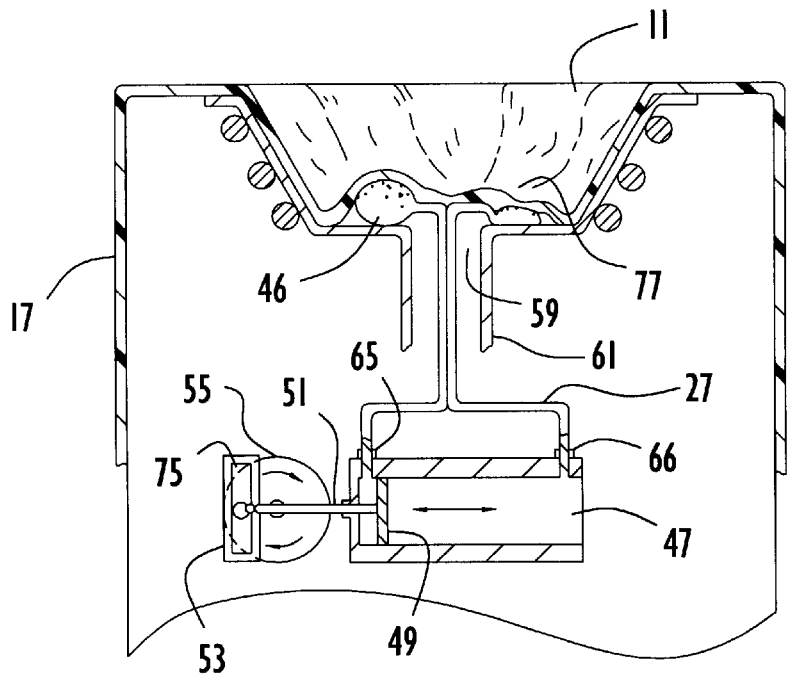
FIGS. 8a–8c are elevational views in partial section of the bladder and basin of FIG. 7a covered by a surgical drape illustrating the sequence of inflation and deflation of the individually inflatable sections according to the present invention.
Figure 8B:
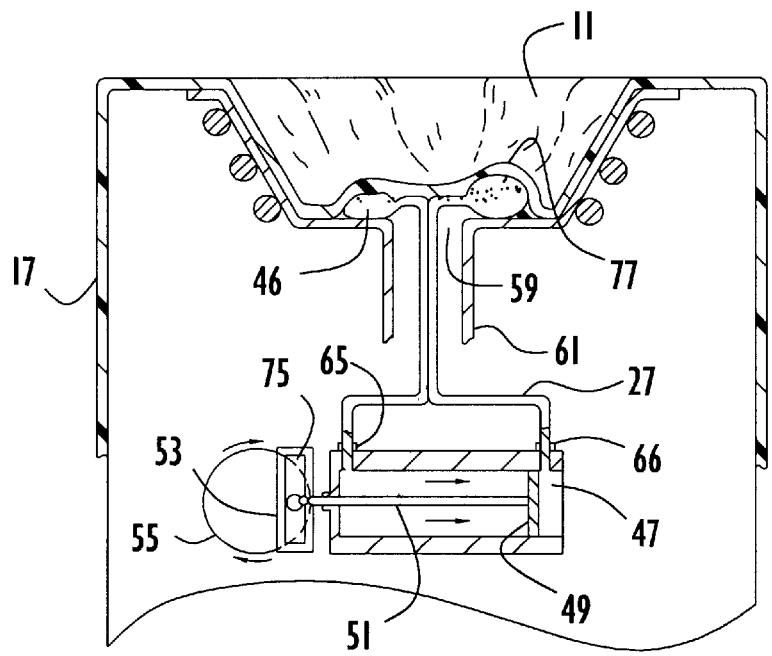
Figure 8C:
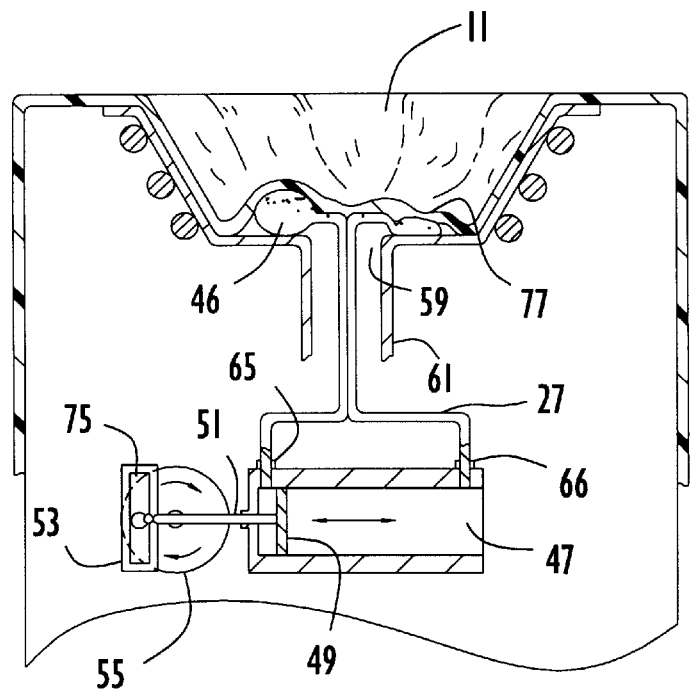

The operation of manipulating drape 17 covering inflatable bladder 23 is now described with reference to FIGS. 8a–8c. Initially, piston 49 is positioned at the proximal end of chamber 47 adjacent port 65 with individual section 46 already inflated due to the resulting compression of air in that section by the piston. Drive wheel 55 rotates in a clockwise direction to drive piston 49 toward the distal end of chamber 47 as described above. As piston 49 is driven toward the distal end of chamber 47, a suction force is created at port 65 to transfer fluid from inflatable bladder section 46 through port 65 to the proximal end of the chamber. Conversely, in the portion of chamber 47 on the distal side of piston 49, fluid is forced through port 66 at the distal end of the chamber to begin inflation of section 77. Similarly, as drive wheel 55 further rotates, piston 49 is driven back towards the proximal end of chamber 47, creating a suction to transfer fluid from inflatable section 77 through port 66 to the distal end of the chamber. In the proximal portion of the chamber, fluid is forced through port 65 to re-inflate section 46. The sections are alternately inflated and deflated in this manner to manipulate the drape toward and away from the basin walls to dislodge the congealed liquid formed on the drape. Alternatively, the bladder may be disposed integrally with the bottom of a drape receptacle or a pre-formed container portion of the drape to manipulate the drape in substantially the same manner described above.

Figure 9A:
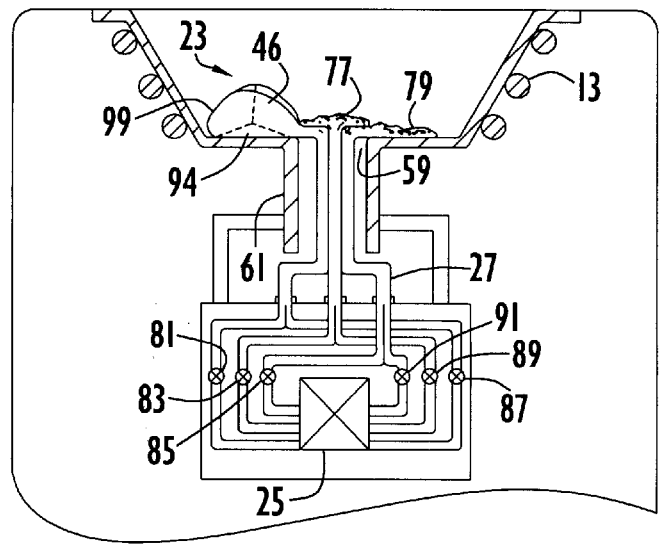
FIG. 9a is an elevational view in partial section of a bladder with three individually inflatable sections disposed at the lowermost portion or bottom of a basin in a surgical slush machine having a pump including multi-lumen tubing and solenoids for inflating and deflating the individually inflatable sections according to the present invention.
Figure 9B:
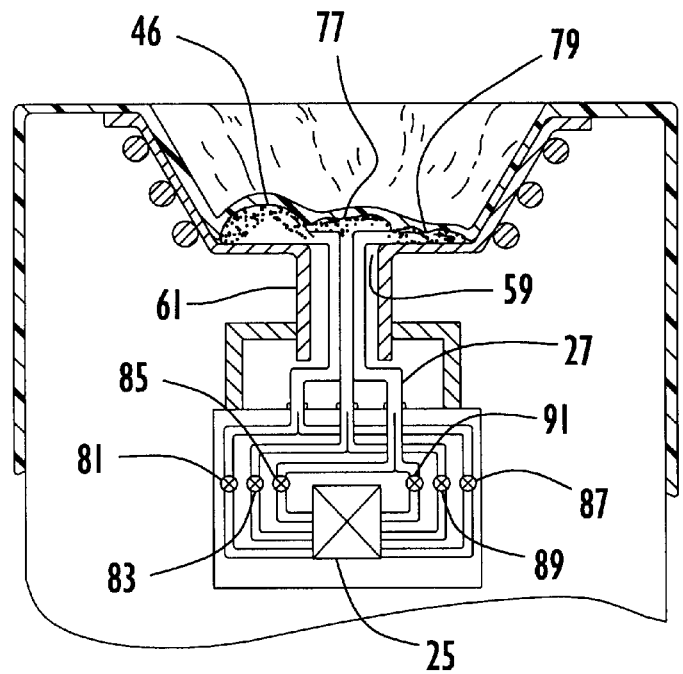
Figure 9C:
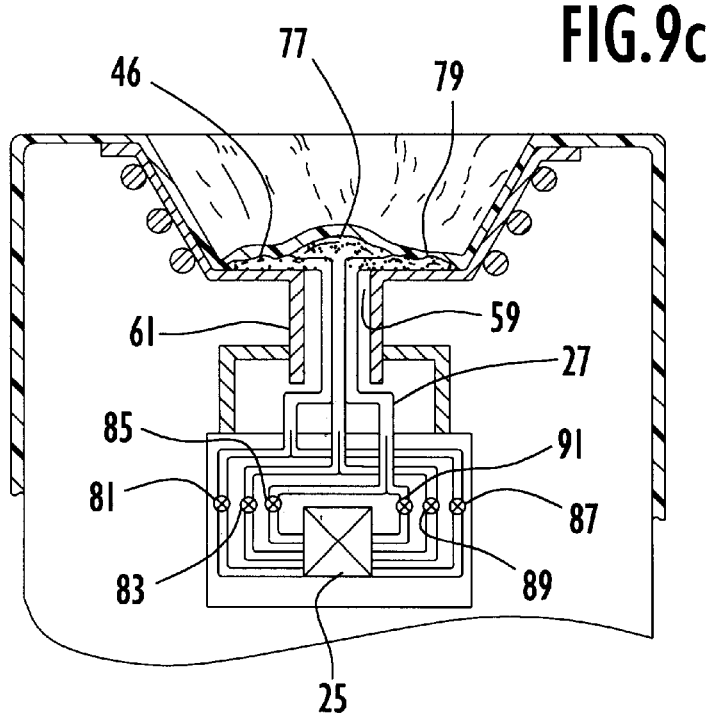

A bladder including three (or more) individually inflatable sections may be employed to manipulate the drape relative to the basin and dislodge the congealed liquid in the manner illustrated in FIG. 9a. Specifically, the drape (not shown) and bladder 23 are substantially similar to the drape and bladder described above for the bladder having two inflatable sections except that bladder 23 includes three individually inflatable sections 46, 77, 79 disposed at the bottom of basin 11. Inflatable sections 46, 77, 79 are connected via hoses or feeds 27 through solenoid-actuated pressure valves 81, 83, 85, and solenoid-actuated suction valves 87, 89, 91 to pump 25. Hoses 27 are preferably multi-lumen tubing but may be conventional or the other types of hoses or feeds. Valves 81, 83, 85, 87, 89, 91 are selectively actuable to control fluid flow by either allowing or cutting off the flow through respective hoses or feeds 27. Individual sections 46, 77, 79, in their fluid expanded state, have a shape substantially similar to a one-third portion of a substantially annular bladder (i.e., each approximately one-hundred and twenty degrees around) and a cross-section including a flat base 94 adjacent the basin floor and extending from the basin wall to the approximate basin center. Base 94 is connected to an upper portion or body 99 in the form of a large arc of the same general type described above. Inflatable sections 46, 77, 79 individually expand when inflated such that the highest point of the inflated section relative to the base is approximately one-half the depth of the basin. Each individual section 46, 77, 79 further includes a respective hose or feed 27 which may be integral with, or attached to, the individual sections. Each hose 27 extends from a corresponding individual section and traverses opening 59 and hose shaft 61 in substantially the same manner described above for the bladder having two inflatable sections except that the hose or feed is divided into two separate paths subsequent to traversing hose shaft 61. A first path traverses a solenoid-actuated pressure valve and enables inflation of the corresponding individual section while a second path traverses a solenoid actuated suction valve and enables deflation of that section. Both paths terminate at the respective pressure and suction interfaces of pump 25. Pump 25 is a conventional pump for accepting fluid through an intake (suction side) and projecting fluid through an out take (pressure side).

The valves are triggered such that one pressure valve and one suction valve are actuated at any one time. The actuating of the valves in this fashion enables the inflatable sections to be inflated and deflated one section at a time in sequential order, thereby manipulating different drape sectors toward and away from the basin walls to dislodge the congealed liquid. The valves, in effect, permit the pump to project fluid out through only one path to a selected deflated section on the pressure side and accept fluid through only one path from a selected inflated section on the suction side to respectively inflate and deflate the individual sections.

Figure 9E:
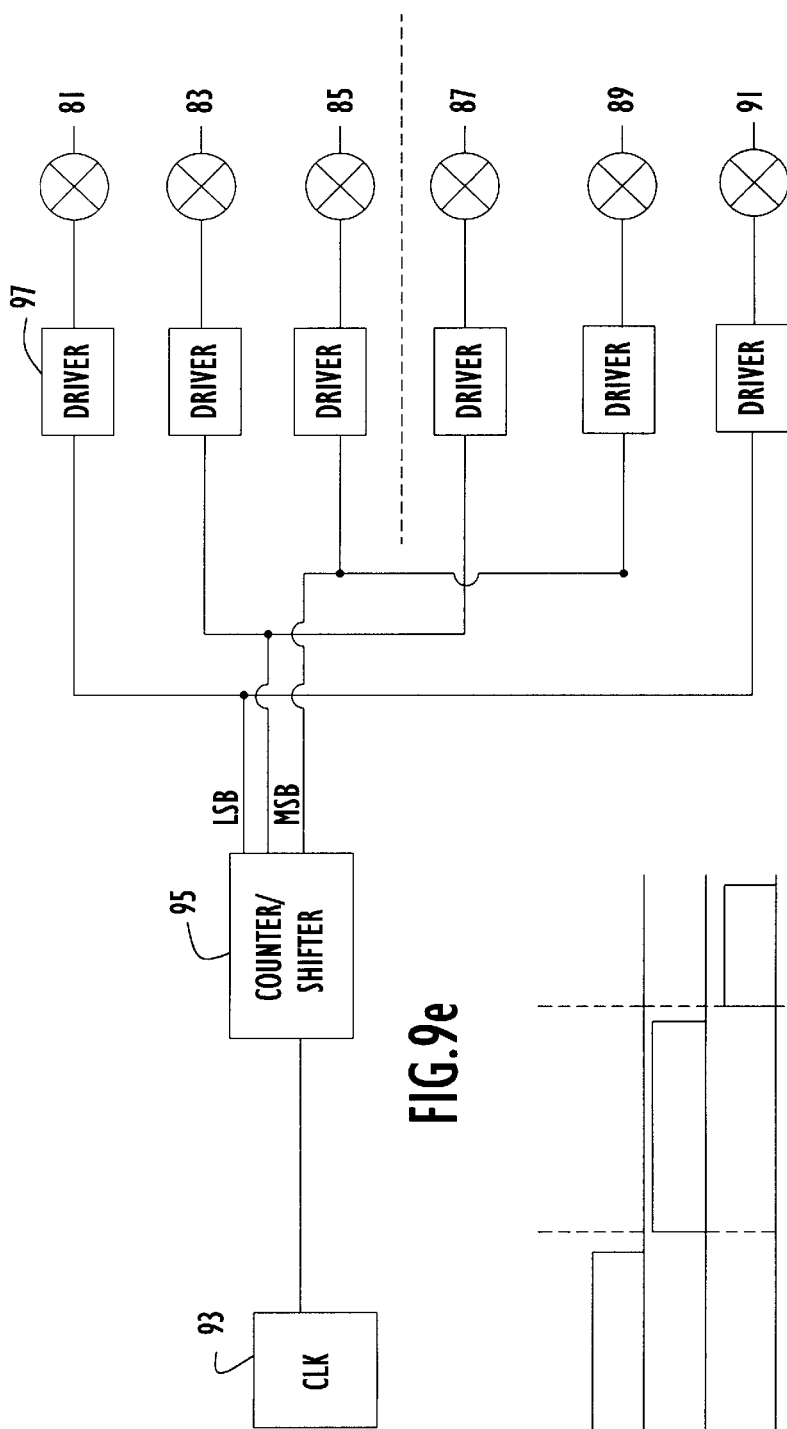
FIG. 9e is an electrical schematic diagram of an exemplary circuit controlling the solenoids of the surgical slush machine of FIG. 9a according to the present invention.

The triggering mechanism for the valves may be any of a number of mechanical or electrical devices. By way of example, a circuit for controlling the valves to operate in accordance with the present invention is illustrated in FIG. 9e. Specifically, each valve 81, 83, 85, 87, 89, 91 is connected to a respective solenoid or other valve actuating driver 97 for actuating the particular valve. Drivers 97 receive an actuating signal from counter 95 triggered by clock 93. Counter 95 may be a wrap-around/modulus counter periodically incrementing the count after a certain period of time, or a circular shifter shifting bits periodically based on the clock signal. For example, the counter may be a three-bit counter wrapping around a count of four with the actuation of the solenoids occurring on the counts one, two and four based on only one of the bits in the count being set as described below (i.e., a count value of three may be masked by combinational logic to prevent actuation of the solenoids while a count of zero has no bits set and does not actuate the solenoids). Further, a three-bit shifter may be employed starting with a value of one and shifting left circularly through the value of four such that the shifter output results in either one, two or four to actuate the solenoids as described below. Alternatively, the shifter may start with a value of four and circularly shift right, or the counter may count in reverse, to achieve the same output and result in a reverse inflation and deflation sequence for the sections.

Figure 9F:
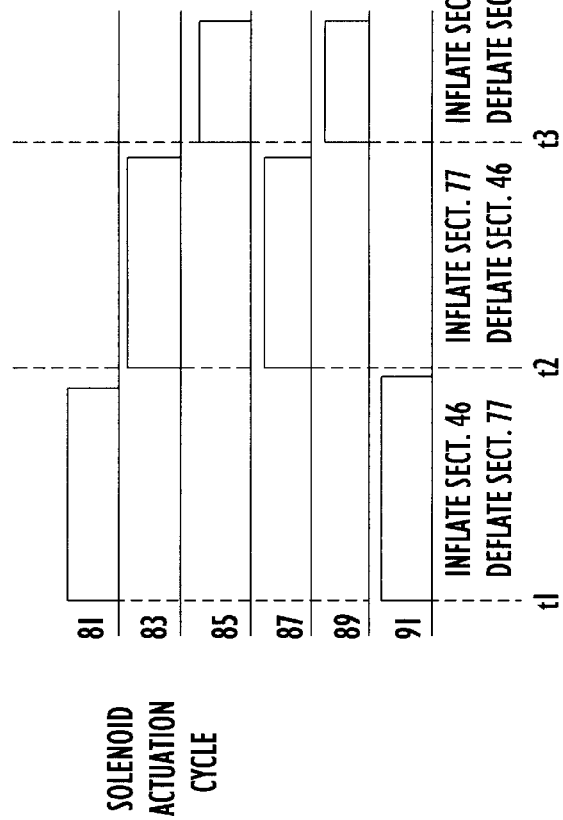
FIG. 9f is a timing diagram illustrating the actuation of the solenoids of the surgical slush machine of FIG. 9a in accordance with the exemplary circuit of FIG. 9e according to the present invention.

The bits from either the count or resultant word from the shifted bits enable actuation of only a single pair of valves (including one suction and one pressure valve) based on a lone bit being set. Specifically, drivers 97 are connected in pairs to one of the output bits of counter or shifter 95. Drivers 97 are paired such that each pair includes drivers corresponding to one pressure and one suction valve. The activation of the particular pair of drivers therefore enables inflation and deflation of the proper corresponding inflatable bladder sections. Since the output from counter or shifter 95 has only a single bit set (i.e., values of one, two or four), only a single pair of valves is actuated at any one time to inflate and deflate the proper sections. The specific cycle of valve actuations is illustrated in FIG. 9f and described below. The exemplary circuitry actuates each pair of valves (pressure and suction) ten times per minute (i.e., 0.16 Hz) to enable proper inflation and deflation of the individually inflatable sections for manipulation of the drape.

Referring to FIGS. 9b–9f, the inflation and deflation operation of the individual sections is now described. Initially, individual section 46 is inflated with sections 77, 79 deflated corresponding to an output of one from counter or shifter 95 (i.e., actuation of pressure solenoid 81 and suction valve 91). Subsequent to inflation of section 46, pressure valve 81 and suction valve 91 are deactivated while pressure valve 83 and suction valve 87 are activated based on an output of two from counter or shifter 95. Suction valve 87 enables deflation of section 46 while pressure valve 83 enables inflation of section 77 via pump 25. Subsequent to inflation of section 77, pressure valve 83 and suction valve 87 are deactivated while pressure valve 85 and suction valve 89 are activated based on an output of four from counter or shifter 95. Suction valve 89 enables deflation of section 77 while pressure valve 85 enables inflation of section 79 via pump 25. The individually inflatable sections are thus inflated one section at a time in sequential order to manipulate the drape relative to, and away from, the basin walls to remove congealed liquid from the sides of the drape as described above. The aforementioned cycle continuously repeats for automatic dislodgement of the congealed liquid. Further, the bladder may include any number of individually inflatable sections in various shapes and may be disposed within a pre-formed container portion of the drape to operate in substantially the same manner described above.

It will be appreciated that the embodiments described above and illustrated in the drawings represent only a few of the many ways of implementing a surgical drape for use with surgical slush machines having automatic dislodgement of congealed liquid.

The surgical drapes may include any material and be of any thickness suitable for constructing pre-formed container portions and maintaining sterility of the sterile media in the basin. The basin and pre-formed container portion of the drape may be of any shape capable of collecting and accessing the sterile media. The pump may be any device capable of alternately inflating and deflating through any number of autonomously selected lines. The orientation of the pumping mechanism may be any orientation capable of pumping the fluid and fitting in the desired space (e.g., inside cabinet, on a shelf next to cabinet etc.). Further, the selection of the lines used by the pump may be controlled by any mechanical or electrical device capable of periodic actuation of the selected lines. Moreover, the inflation and deflation modes of the pump utilizing opposing polarities of voltage may be controlled by any mechanical or electrical control devices, microprocessors, combinational logic or other circuitry capable of controlling a pump or bellows. In addition, all of the aforementioned inflatable embodiments may be implemented using any type of fluid (i.e., gas or liquid) capable of inflating the embodiments sufficiently to dislodge the congealed sterile liquid.

The pre-formed container portion may include any number of individual fluted sections arranged in any configuration that generally conforms to the shape of the particular basin. The drapes may be used in any type of thermal treatment system for generating slush or heating liquid, or as generic liners for any type of basin. The inflatable bladders may be premolded into the drape or be a separate unit attached to the drape by any conventional attachment processes. In addition, the drapes may be utilized for use with thermal treatment systems having a plurality of basins recessed in a top surface for cooling and/or heating a sterile medium wherein the drapes include a plurality of pre-formed container portions or are formed into a plurality of drape receptacles corresponding to the plurality of basins with the aforementioned bladders, ridges, and fluted sections disposed in the container portions, drape receptacles and/or basins, as described above, of only those basins cooling the sterile medium. The stirrups of the drape may be made of elastic, rubber-band like or any other suitable material shaped in any manner capable of securing the stirrups to the system.

From the foregoing description it will be appreciated that the invention makes available a novel surgical drape for use with surgical slush machines for forming and collecting surgical slush by dislodgement of congealed liquid wherein a sterile drape may be utilized with and/or include deformities such as wrinkles, individual fluted sections, a substantially annular inflatable bladder, the combination of the substantially annular bladder and individual fluted sections, or a bladder including a plurality of individually inflatable sections.

Having described preferred embodiments of a new and improved method and apparatus for a surgical drape for use in forming and collecting surgical slush, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An apparatus for thermally treating a sterile medium comprising:

a system housing including a top surface;

a basin recessed in said top surface of said housing for transferring thermal energy to said sterile medium;

a drape covering and hanging down from said top surface of said housing with a portion of said drape disposed in said basin for collecting said sterile medium;

thermal treatment means in thermal relation with said basin for thermally treating said sterile medium such that said sterile medium congeals and adheres to said drape adjacent walls of said basin;

manipulation means disposed in said basin for automatically manipulating said drape wherein said manipulation means includes a plurality of individually inflatable sections; and pump means for inflating and deflating said individually inflatable sections in sequential order to manipulate said drape relative to said basin and dislodge said congealed sterile medium from said drape.

2. The apparatus of claim 1 further including:

a plurality of basins recessed in said top surface of said housing for containing said sterile medium, wherein said thermal treatment means thermally treats a portion of said basins to congeal said sterile medium; and a plurality of said manipulation means wherein each said manipulation means is disposed in one of said basins thermally treated to congeal said sterile medium;

wherein said pump means inflates and deflates said plurality of manipulation means to manipulate said drape and dislodge congealed sterile medium in said basins congealing said sterile medium.

3. The apparatus of claim 1 wherein said pump means further includes:

a chamber;

connection means for connecting each of said individually inflatable sections to said chamber;

a piston disposed within said chamber; and drive means for driving said piston within said chamber in a reciprocating manner such that said reciprocating motion of the piston within the chamber alternately inflates and deflates each said individually inflatable section of said manipulation means one section at a time in sequential order.

4. The apparatus of claim 1 further including:

pump connection means for connecting each of said individually inflatable sections to said pump means via a first and second path, said first path establishing a connection for inflating said individually inflatable sections and said second path for establishing a connection to deflate said individually inflatable sections;

solenoid means disposed within said pump connection means for controlling said inflation and deflation of said individually inflatable sections; and solenoid control means for selectively actuating said solenoid means to inflate and deflate said individually inflatable sections one section at a time in sequential order.

5. In the apparatus of claim 1, a method of dislodging congealed sterile medium adhering to said drape adjacent walls of said basin comprising the step of:

(a) inflating and deflating said individually inflatable sections in sequential order one section at a time via said pump means to manipulate said drape relative to said basin and dislodge said congealed sterile medium adhering to said drape adjacent walls of said basin.

6. The method of claim 5 wherein said apparatus further includes:

a plurality of basins recessed in said top surface of said housing for containing said sterile medium wherein said thermal treatment means thermally treats a portion of said basins to congeal said sterile medium;

a plurality of said manipulation means wherein each of said manipulation means is disposed within said basins thermally treated to congeal said sterile medium, and step (a) further includes:

(a.1) inflating and deflating each of said manipulation means to manipulate said drape relative to said basins congealing said sterile medium to dislodge said congealed sterile medium.

7. The method of claim 5 wherein said pump means is connected to said individually inflatable sections and includes a piston disposed within a chamber for inflating and deflating said individually inflatable sections, and step (a) further includes:

(a.1) reciprocating said piston within said chamber to inflate and deflate each of said individually inflatable sections.

8. The method of claim 5 wherein said apparatus further includes connection means for connecting each of said individually inflatable sections to said pump means via a first path for inflation and a second path for deflation, and solenoid means for selectively controlling said inflation and deflation, wherein step (a) further includes:

(a.1) selectively actuating said solenoid means for establishing said first and second paths to inflate a first individually inflatable section and deflate a second previously inflated individually inflatable section such that said individually inflatable sections are inflated one section at a time in sequential order to manipulate said drape relative to said basin and dislodge said congealed sterile medium.

9. An apparatus for thermally treating a sterile medium comprising:

a system housing including a top surface;

a basin recessed in said top surface of said housing for transferring thermal energy to said sterile medium;

a drape covering and hanging down from said top surface of said housing with portion of said drape disposed in said basin for collecting said sterile medium;

thermal treatment means in thermal relation with said basin for thermally treating said sterile medium such that said sterile medium congeals and adheres to said drape adjacent walls of said basin;

an annular bladder disposed in said basin for automatically manipulating said drape; and pump means for inflating and deflating said annular bladder to manipulate said drape relative to said basin and dislodge said congealed sterile medium from said drape.

10. The apparatus of claim 9 further including:

a plurality of basins recessed in said top surface of said housing for containing said sterile medium, wherein said thermal treatment means thermally treats a portion of said basins to congeal said sterile medium; and a plurality of said annular bladders wherein each said annular bladder is disposed in one of said basins thermally treated to congeal said sterile medium.

11. In a thermal treatment system including a basin recessed in a top surface of a system housing for congealing a sterile medium, a drape for maintaining sterility of said sterile medium having a first portion covering said housing and hanging down from said top surface and a second portion disposed in said basin for collecting said sterile medium, manipulation means disposed between the drape and the bottom of the basin for manipulating said drape, wherein said manipulation means includes a plurality of individually inflatable sections, and pump means for inflating and deflating said manipulation means, a method for dislodging congealed sterile medium adhering to said drape adjacent walls of said basin comprising the step of:

(a) inflating and deflating said individually inflatable sections in sequential order one section at a time via said pump means to manipulate said drape relative to said basin and dislodge said congealed sterile medium adhering to said drape adjacent walls of said basin.

12. The method of claim 11 wherein said system further includes:

a plurality of basins recessed in said top surface of said housing for containing said sterile medium wherein said thermal treatment means thermally treats a portion of said basins to congeal said sterile medium;

a plurality of said manipulation means wherein each of said manipulation means is disposed within said basins thermally treated to congeal said sterile medium, and step (a) further includes:

(a.1) inflating and deflating each of said manipulation means to manipulate said drape relative to said basins congealing said sterile medium to dislodge said congealed sterile medium.

13. The method of claim 11 wherein said pump means is connected to said individually inflatable sections and includes a piston disposed within a chamber for inflating and deflating said individually inflatable sections, and step (a) further includes:

(a.1) reciprocating said piston within said chamber to inflate and deflate each of said individually inflatable sections.

14. The method of claim 11 wherein said system further includes connection means for connecting each of said individually inflatable sections to said pump means via a first path for inflation and a second path for deflation, and solenoid means for selectively controlling said inflation and deflation, wherein step (a) further includes:

(a.1) selectively actuating said solenoid means for establishing said first and second paths to inflate a first individually inflatable section and deflate a second previously inflated individually inflatable section such that said individually inflatable sections are inflated one section at a time in sequential order to manipulate said drape relative to said basin and dislodge said congealed sterile medium.

* * * * *